United States Patent [19]

Backlund et al.

[11] Patent Number: 4,686,304

[45] Date of Patent: Aug. 11, 1987

[54] CARBAMATE COMPOUNDS

[75] Inventors: Stephen J. Backlund, Fair Oak; Robert E. Olsen, Placerville, both of Calif.

[73] Assignee: United States of America, Washington, D.C.

[21] Appl. No.: 341,123

[22] Filed: Jan. 20, 1982

Related U.S. Application Data

[63] Continuation of Ser. No. 182,632, Aug. 29, 1980, Pat. No. 4,337,196.

[51] Int. Cl.$^4$ .......................................... C07C 125/073
[52] U.S. Cl. .................................................... 560/25
[58] Field of Search ...................................... 560/25

[56] References Cited

FOREIGN PATENT DOCUMENTS 107600 12/1965 Norway ............................... 560/25

OTHER PUBLICATIONS

Khan et al., Jour. of Medicinal Chem., vol. 19, (1976), pp. 313–317.

Primary Examiner—Bernard Helfin
Attorney, Agent, or Firm—Donald E. Egan

[57] ABSTRACT

The invention provides compounds of the formula

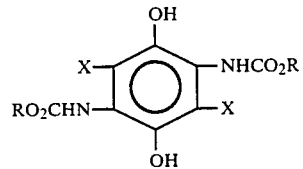

wherein X is chloride, fluoride, bromide, iodide or alkoxy, and R is alkyl, arylalkyl, or phenyl which compounds are intermediates in the preparation of 3,6-bis(-carboethoxyamino)-2,5-diaziridinyl-1,4-benzoquinone.

3 Claims, No Drawings

CARBAMATE COMPOUNDS

This application is a division of application Ser. No. 182,632, filed 8-29-80 and now U.S. Pat. No. 4,337,196.

FIELD OF INVENTION

The present invention is directed to a new method for the preparation of 3,6-bis(carboethoxyamino)-2,5-diaziridinyl-1,4-benzoquinone, hereinafter sometimes referred to as "AZQ". The present invention also contemplates the reaction of a dialkylpyrocarbonate with a diamino hydroquinone to form a new compound, e.g., 2,5-dichloro-3,6-bis(carboethoxyamino)-1,4-hydroquinone, which may be used as an intermediate in the preparation of the AZQ or which may be used for other purposes, such as in a bactericide or a fungicide.

DESCRIPTION OF THE PRIOR ART

AZQ or 3,6-bis(carboethoxyamino)-2,5-diaziridinyl-1,4-benzoquinone is known in the prior art (see for example U.S. Pat. No. 2,913,453). The use of AZQ as an anti-cancer drug has also been described in the prior art (see for example U.S. Pat. No. 4,146,622 and A. H. Khan and J. S. Driscoll, J. Med. Chem., 19, 313 (1976)).

All synthesis of AZQ reported in the prior art required the preparation of a bis-urethane intermediate, i.e., 2,5-dichloro-3,6-bis(carboethoxyamino)-1,4-benzoquinone (Compound IV, below). The treatment of the bis-urethane intermediate with ethylenimine produces AZQ in good yield, but the prior art synthesis of the bis-urethane intermediate produced only low and variable yields.

The original synthesis of the bis-urethane intermediate described in the prior art employed the reaction of chloranil with urethane and metallic sodium. This procedure produced yields of the bis-urethane ranging from 0–27%. In addition to the low yields, the procedure required that the chloranil be added all at once (exothermic reaction) and that the excess metallic sodium be decomposed with water. Thus, the reaction presented safety problems on scale-up in addition to the low and variable yields.

More recently, von Gizycki, Angew. Chem. International Ed., 10 403 (1971) reported that treatment of 2,5-dichloro-3,6-diamino-1,4-benzoquinone with oxalyl chloride produced the diisocyanato compound which may be reacted with ethanol to produce the bis-urethane intermediate. However, the overall yield of the bis-urethane intermediate by this procedure was only 17% and the reaction requires refluxing a dilute solution of the starting material with a large excess of oxalyl chloride for at least two days.

The present invention produces AZQ through the use of a novel intermediate compound, namely, 2,5-dichloro-3,6-bis(carboethoxyamino)-1,4-hydroquinone, which is prepared by the reaction of diethyl pyrocarbonate with 2,5-dichloro-3,6-diamino-1,4-hydroquinone. Although diethyl pyrocarbonate is known to carboethoxylate amines and phenols (see L. Rosnati, Ber., 96, 3098 (1963); Chem. Abstr., 60, 1572 (1964); J. Larrouguere, Bull. Soc. Chim. Fr., 1543 (1964); Chem. Abstr., 61, 10769 (1964); J. Larrouguere, Bull. Soc. Chim. Fr., 2972 (1965); Chem. Abstr., 64, 3392 (1966); and A. Muhlrad, G. Hegyi, and G. Toth, Acta Biochim. Biophys., 2, 19 (1967)), diethyl pyrocarbonate is relatively stable in absolute ethanol and its reaction with amines and phenol is pH dependent. Alkaline conditions are reported to favor both the reaction of amines and phenols with diethyl pyrocarbonate. Phenols have been found to react over a range of pH 7.5–9 while amines react over a range of pH 4–9. It has also been reported that amino acids are carboethoxylated with diethyl pyrocarbonate in refluxing ethanol under neutral conditions.

We have now found that diamino dichloro hydroquinone reacts with diethyl pyrocarbonate in refluxing ethanol only at the amine function to produce 2,5-dichloro-3,6-bis(carboethoxyamino)-1,4-hydroquinone. In ethyl acetate or under alkaline conditions in ethanol, diethyl pyrocarbonate does react to some extent at the alcohol function of 2,5-dichloro-3,6-diamino-1,4-hydroquinone. However, diamino dichloro benzoquinone does not react with diethyl pyrocarbonate either in refluxing ethanol or in neat solution of diethyl pyrocarbonate at reflux.

The present invention produces AZQ by the use of a novel intermediate compound, namely, 2,5-dichloro-3,6-bis(carboethoxyamino)-1,4-hydroquinone in high yields with short reaction times which do not require either large excesses of solvents or reagents. As a result, the present invention provides a new and improved method for the production of AZQ which results in substantially lower costs, shorter processing time, improved reliability, and significantly simplified processing.

BRIEF DESCRIPTION OF THE PRESENT INVENTION

The starting material for the method of the present invention is a tetra-substituted benzoquinone, preferably the tetra-chloro derivative known as chloranil. Although the chloranil is preferred, the chlorine, bromine, iodide, or akloxy-substituents may be used. In the first step, the chloranil is treated with ammonium hydroxide to produce 2,5-dichloro-3,6-diamino-1,4-benzoquinone (Compound I) as shown in reaction 1.

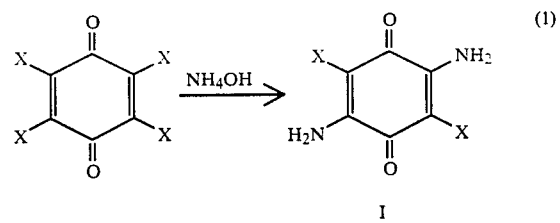

Wherein X may be chlorine, fluorine, bromine, iodine or alkoxy groups.

Compound I is next reduced to produce 2,5-dichloro-3,6-diamino-1,4-hydroquinone (Compound II). This reaction is shown below as reaction 2.

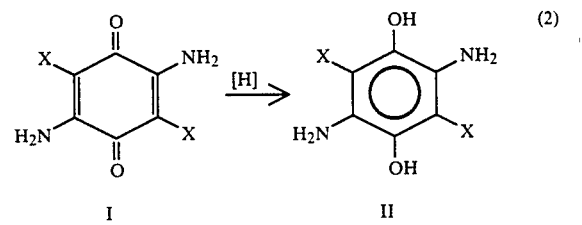

Compound II is then reacted with an excess of diethyl pyrocarbonate to yield 2,5-dichloro-3,6-bis(carboethoxyamino)-1,4-hydroquinone (Compound III) which is shown in reaction 3 below.

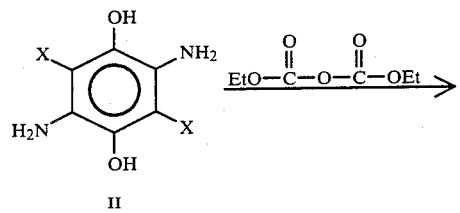
(3)

Compound III is next oxidized to form 2,5-dichloro-3,6-bis(carboxyethoxyamino)-1,4-benzoquinone, (Compound IV) as is shown below in reaction 4.

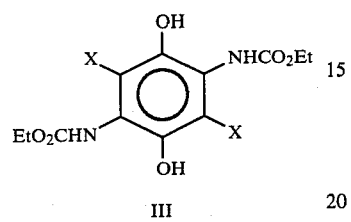
(4)

Compound IV is finally reacted with a suitable azirodinyl compound to produce AZQ (Compound V) or a derivative thereof, as is shown in reaction 5 below.

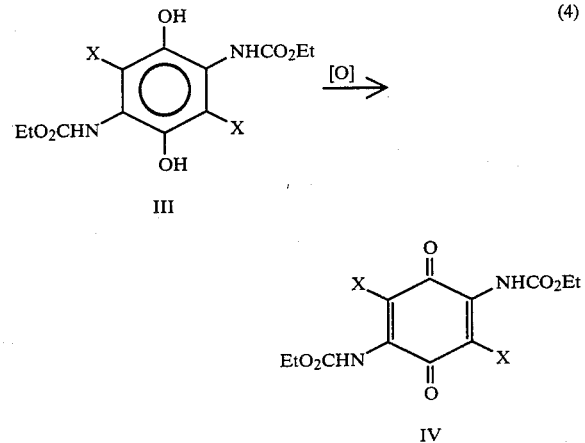

$R^1$, $R^2$, $R^3$, $R^4$=H and/or alkyl.

The series of reactions 1-5 shown above are applicable to fluoro, bromo, iodo, and alkoxy derivatives of I (X=F, Br, I, OR) in addition to the aforementioned chloro derivative (X=Cl). Substituted aziridinyl groups can also be introduced onto the benzoquinone via the above method. It is also feasible to prepare naphthyl derivatives (i.e., VI) by this method.

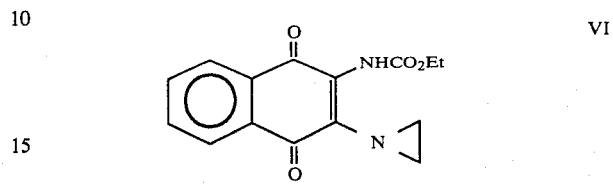
VI

DETAILED DESCRIPTION OF THE PRESENT INVENTION

The chemistry used in the synthesis of the compounds of interest is based mainly on the reaction of tetrachlorobenzoquinone, also known as chloranil, and its tetrafluoro analog, fluoranil. Chloranil may be obtained in a well-known manner from phenol, p-chlorophenol or p-phenylenediamine by treatment with potassium chlorate and hydrochloric acid. Fluoranil is prepared from chloranil by reaction with calcium fluoride at elevated temperatures.

1. PREPARATION OF 3,6-DIAMINO-1,4-BENZOQUINONES

The first step in the synthesis is the replacement of one pair of the substituents of the benzoquinone with a pair of amine groups, which is preferably carried out by reacting ammonium hydroxide with the tetra-substituted quinone derivative.

This reaction is known in the prior art. Two reports have appeared in the literature for the preparation of 2,5-dichloro-3,6-diamino-1,4-benzoquinone I from chloranil and ammonia. In French Pat. No. 1577091 (Aug. 1, 1969) Geigy reported that use of an aprotic solvent (acetonitrile) gave a near quantitative yield of the diamino benzoquinone (I). Fieser (*J. Am. Chem. Soc.*, 57 1844 (1935), had earlier reported its preparation in 75% yield using alcohol as the solvent. We have found that these two procedures produce different products when analyzed by TLC. However, both compounds have identical infrared (KBr pellet) and proton NMR spectra (DMSO). The acetonitrile-prepared material is apparently the desired I while the alcohol-prepared material is its tautomer VII.

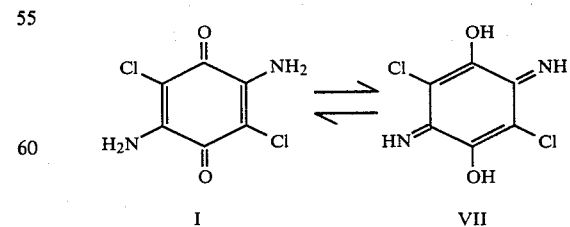

Compound I may be converted into VII by washing with water or alcohol while compound VII may be converted into I by dissolving it in DMSO or by Soxhlet extraction with acetonitrile.

Gizycki developed a procedure to prepare I from chloranil employing concentrated ammonium hydroxide instead of ammonia and using methoxyethyl acetate as the solvent. This procedure gives pure I and eliminates the processing difficulties found in the previous procedures.

The preparation of 3,6-diamino-1,4-benzoquinones is not limited to the chloro derivative I. Tetrahalo-1,4-benzoquinones and tetraalkoxy-1,4-benzoquinones react with ammonia and amines in general to produce the various diaminoquinones. Reactions of the tetra-substituted quinones have been well documented for fluoro, chloro, bromo, and alkoxy derivatives (see E. Winkelmann, *Tetrahedron*, 25, 2427 (1969); K. Wallenfels and W. Draber, *Chem. Ber.*, 93, 3070 (1960); K. Wallenfels and W. Draber, *Ann.* 667, 55 (1963); R. Neeff and O. Bayer, *Chem. Ber.*, 1137 (1957); and British Pat. No. 762723 (Dec. 5, 1956)). It is contemplated that the reaction of iodonil (X=I) with amines (or ammonia) would behave similarly since it gives similar results when treated with alkoxides.

The reaction of the ammonium hydroxide with the quinone derivatives, the reactive halogen of which is to be exchanged for a base radical, is best carried out in solvents or diluents. Since the halogen is split off in the form of hydrogen halide, it proves advisable to use at least 2 moles of the amine per halogen atom in order to provide hydrohalic acid acceptor. The reactions generally proceed spontaneously with evolution of heat; where this is not the case, mild heating is sufficient. If a proper diluent has been chosen, the new quinone derivative will crystallize directly from the reaction mixture in the course or at the end of the reaction, while the diamine hydrohalide remains in solution. The lower alcohols often serve this purpose.

2. REDUCTION OF 2,5-DICHLORO-3,6-DIAMINO-1,4-BENZOQUINONE TO 2,5-DICHLORO-3,6-DIAMINO-1,4-HYDROQUINONE

The reduction of I to II was found to be most conveniently accomplished using sodium dithionite. Under optimal conditions, yields of 90–95% were obtained. Increasing the temperature of reaction much above 30° C. tends to decrease the yield of II. It is necessary to acidify the reaction mixture after treatment of I with $Na_2S_2O_4/NH_4OH$ otherwise the product obtained will react with diethyl pyrocarbonate to a large extent at the hydroxyl function of the hydroquinone. The product (II) is extremely sensitive to air oxidation under basic conditions, but much less so under acidic conditions. Due to the sensitivity of II to air oxidation, it was found to be advantageous not to dry the product, but instead to use the wet-product, after washing with ethanol, in the subsequent reaction with diethyl pyrocarbonate. However, the amount of diethyl pyrocarbonate was increased to 1.5 equivalents (instead of 1.1 equiv.) in order to accommodate any decomposition of the diethyl pyrocarbonate due to small amount of water which might be left in the wet II after washing with ethanol.

Because the benzoquinones and hydroquinones are rather closely balanced energetically, it is generally relatively easy to interconvert them.

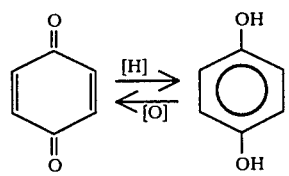

A large number of reagents have been used for the reduction of benzoquinones and the oxidation of hydroquinones, and there are certainly many more which could have been used but which have not been reported.

Benzoquinones have been reduced by sodium dithionite, sodium thiosulfate, sodium sulfite, sulfur dioxide, hydrogen iodide, stannous chloride, zinc and hydrochloric acid, Raney nickel and hydrogen, and lithium aluminum hydride (see French Pat. No. 1544504 Oct. 31, 1968, and British Patent (No. 1,130,275 Oct. 16, 1968). Also, a number of benzoquinones have been utilized as oxidizing agents for other organic compounds, therefore, a large number of organic compounds could be considered as reducing agents for benzoquinones.

Specifically, sodium dithionite was used as early as 1935 to reduce diamino dichloro benzoquinone to the hydroquinone in a purification scheme of diamino dichloro benzoquinone.

3. 2,5-DICHLORO-3,6-BIS(CARBOETHOXYAMINO)-1,4-HYDROQUINONE

The present invention broadly contemplates the reaction of a di-substituted pyrocarbonate with a diamino hydroquinone to form a dialkyl, a di(aryalkyl), a diphenyl, or a substituted diphenyl diaminohydroquinone-N,N'-dicarboxylate. In addition to the preferred diethyl pyrocarbonate, the present invention contemplates the use of pyrocarbonates di-substituted with alkyl groups [having up to twelve (12) carbons, or more[, aryalkyl groups (such as benzyl or substituted arylalkyl), phenyl and substituted phenyl groups. The heretofore unknown 2,5-dichloro-3,6-bis(carboethoxyamino)-1,4-hydroquinone (III) has been synthesized and utilized as an intermeidate in the preparation of AZQ. Compound III and the other compounds produced by the present invention also have bactericidal and fungicidal properties and may be used as general purpose disinfectants. Compound III is synthesized by treatment of 2,5-dichloro-3,6-diamino-1,4-hydroquinone (II) with diethyl pyrocarbonate. The hydroquinone (III) obtained in reaction 3 above was found to be oxidized to the corresponding benzoquinone IV by oxidizing agents such as nitric acid or hydrogen peroxide.

It has been found that the following variables impact on the yield and purity of Compound III:

1. The mole ratio of the diethyl pyrocarbonate to Compound II.
2. The effect of solvent.
3. The reaction time.

The yields of III obtained by varying the time of reaction and the amounts of diethyl pyrocarbonate and ethanol are shown in Table I below. It can be seen from these results that the yield of III increases as the amount of ethanol is decreased until the amount of ethanol is reduced to 10 ml per 20 mmol of II. Further reduction in the amount of ethanol causes no significant increase in yield. Increasing the amount of diethyl pyrocarbonate increases the yield of III when large amounts of ethanol are utilized, but does not improve the yield if 10 ml or less of ethanol is used per 20 mmol of II. The yield of III reaches a maximum after 4 hours at 80° C. Further heating at 80° C. results in little change in the yield of III.

TABLE I

YIELDS OF 2,5-DICHLORO-3,6-BIS(CARBOETHOXY-AMINO)-1,4-HYDROQUINONE OBTAINED ON REACTION OF 2,5-DICHLORO-3,6-DIAMINO-1,4-HYDROQUINONE (20 MMOL) WITH DIETHYL PYROCARBONATE

| mmol Diethyl Pyrocarbonate | ml Ethanol | Time at 80° C. (hr) | Isolated Yield, % |
|---|---|---|---|
| 44 | 40 | 0.5 | 16 |
| 44 | 40 | 2 | 40 |
| 44 | 40 | 4 | 63 |
| 44 | 40 | 18 | 66 |
| 80 | 40 | 4 | 74 |
| 80 | 20 | 4 | 76 |
| 44 | 10 | 4 | 85 |
| 80 | 10 | 4 | 87 |
| 160 | 0 | 4 | 84 |

If solvents other than ethanol (i.e., ethyl acetate) are utilized, reaction of the diethyl pyrocarbonate at the alcohol function of the hydroquinone may occur to some extent.

Compound III was characterized by IR, NMR, UV, and elemental analysis.

4. OXIDATION OF 2,5-DICHLORO-3,6-BIS(CARBOETHOXYAMINO)-1,4-HYDROQUINONE TO 2,5-DICHLORO-3,6-BIS(CARBOETHOXYAMINO)-1,4-BENZOQUINONE

The best oxidizing agent for the conversion of III to IV was found to be nitric acid. However, in order to prevent the product from floating on the water and foaming out of the reaction flask, it was advantageous to add a surfactant, such as the sodium salt of monotetradecyl sulfate [Tergitol 4 (anionic)]. Concentrated nitric acid (65–70%) was found to rapidly (4 hrs. at 25° C.) and completely oxidize III to IV. Use of less concentrated nitric acid was less satisfactory and sometimes resulted in unoxidized III even after prolonged reaction. Under optimal conditions, III can be oxidized with nitric acid to IV in 95% yield. The oxidation of III to IV with 30% hydrogen peroxide was much slower than that with nitric acid and required heating for an extended period with a co-solvent (i.e., ethanol) and resulted in much lower yields of IV.

In contrast to II, III does not appear to be sensitive to air oxidation. However, it was found to be convenient to wash one ethanol-wet III with water and add it directly to the nitric acid in order to eliminate the time necessary to dry III.

Some of the reagents which may be used to oxidize hydroquinones to benzoquinones are: nitric acid, ferric ion ($FeCl_3$ or $Fe_2(SO_4)_3$), oxygen, silver oxide, manganese dioxide, lead tetraacetate, hydrogen peroxide, chromic acid, chromium trioxide, periodic acid, and potassium chlorate. Hydroquinones may also be oxidized by electrolysis or in some instances even by quinone itself.

5. FORMATION OF THE DIAZIRIDINYL DERIVATIVE

The reaction of ethylenimine or its alkyl substituted derivatives with di-substituted bis(carboethoxyamino)-benzoquinone is taught in the prior art. The reaction of homologs of ethylenimine, such as 2-methylaziridine or 2,2-dimethylaziridine, and the like are contemplated. Generally, the preferred procedure contemplates dissolving the benzoquinone in a suitable solvent, such as THF, and adding thereto an excess of aziridine or its homolog at ambient temperatures. Other procedures known to those skilled in the art may also be used. One suitable procedure is illustrated by Example 4, below. Examples 5 and 6 illustrate the preferred purification steps.

The following examples will serve to illustrate the preparation of AZQ and the intermediate compounds formed thereby, but it is understood that these examples are set forth merely for illustration and many other quinone derivatives may be made through suitable variation. The intermediate III was isolated and characterized in Example 1, but only semi-isolated and then oxidized to IV in Example 3.

EXAMPLE 1

Preparation of 2,5-Dichloro-3,6-Bis(Carboethoxyamino)-1,4-Hydroquinone from 2,5-Dichloro-3,6-Diamino-1,4-Benzoquinone A 500-ml flask maintained under nitrogen was charged with 100 ml (1.48 mol) of concentrated ammonium hydroxide, 100 ml of water, and 41.4 g (0.2 mol) of 2,5-dichloro-3,6-diamino-1,4-benzoquinone (I) and was cooled to 5° C. (ice-water bath). The brown slurry was then treated with 69.6 g (0.400 mol) of sodium dithionite and the temperature rose to 27° C. After cooling the resultant white slurry down to 5° C. (15 min), 100 ml (1.75 mol) of acetic acid was added at 5°–20° C. over a period of 15 minutes. The reaction mixture was cooled to 5° C. and filtered under nitrogen. The resulting 2,5-dichloro-3,6-diamino-1,4-hydroquinone (II) solids were washed twice with 50 ml of water and twice with 50 ml of ethanol while still under nitrogen. The product (II) was transferred to a 500-ml flask under nitrogen which was then charged with 100 ml of ethanol and 97.2 g (0.600 mol) of diethyl pyrocarbonate. The resultant slurry was heated to reflux (80° C.) over a period of 1 hr. and maintained at reflux for 4 hrs. The reaction was then cooled to 5° C. and filtered. The white solids were washed twice with 50 ml of ethanol and dried under vacuum to afford 58.9 g (83% yield) of 2,5-dichloro-3,6-bis(carboethoxyamino)-1,4-hydroquinone, (III) m.p. 234°–235° C. (dec.); IR (KBr pellet) 3380 (OH), 1690 $cm^{-1}$ (C=O); NMR (DMSO-$d_6$) δ9.09 (s, 2H, -OH), 8.58 (s, 2H, NH), 4.06 (q, J=7 Hz, 4H, $CH_2$), 1.21 ppm (t, J=7 Hz, 6H, $CH_3$); $UV_{max}$ (MeOH) 214 (28,092), 308 nm (6,555).

Anal. Calcd. for $C_{12}H_{14}Cl_2N_2O_6$ (353.16): C, 40.81; H, 4.00; N, 7.93; Cl, 20.08; O, 27.18. Found: C, 40.88; H, 4.06; N, 7.92; Cl, 19.94; O, 27.22.

The Examples 2 through 4 will serve to illustrate the preparation of 3,6-bis(carboethoxyamino)-2,5-diaziridinyl-1,4-benzoquinone, but it is understood that many other aziridinyl substituted benzoquinone may be prepared by this procedure.

EXAMPLE 2

2,5-Diamino-3,6-Dichloro-1,4-Benzoquinone (I)

A 100-l. glass reactor was charged with 46.0 kg (45.1 l.) of 98% methoxyethyl acetate and 11.5 kg (53.2 mol) of recrystallized p-chloranil. The well agitated slurry was then heated to 60° C. and the heat source turned off. Next, 18.1 l. (272 mol) of 27% ammonium hydroxide (technical) was charged to the slurry over 30 minutes (exotherm to 107° C.). The reaction mixture was allowed to slowly cool to ambient (maintained at a minimum of 70° C. for 1 hour after the addition is complete). After 22 hours at ambient temperatures the reaction mixture was filtered, washed with water (26 l.), acetone (10 l.) and dried (70° C., 10 mm Hg) to yield 9.21 kg (95.2%) (I).

EXAMPLE 3

3,6-Bis(Carboethoxyamino)-2,5-Dichloro-1,4-Benzoquinone (IV)

A 5.0-l. flask maintained under nitrogen was charged with 1.0 l. (14.8 mol) of concentrated ammonium hydroxide and 1.0 l. of water. This solution was cooled to 5° C. (ice-water bath), 414 g (2.00 mol) of I was added, and the brown slurry was treated with 696 g (4.0 mol) of sodium dithionite while maintaining the temperature below 30° C. After cooling the resulting white slurry down to 5° C. (30 min.), 1.0 l. (17.5 mol) of glacial acetic acid was added at 5°-30° C. over a period of 20 minutes. The reaction was then cooled to 10° C. and filtered under nitrogen. The resulting 2,5-dichloro-3,6-diamino-1,4-hydroquinone (II) solids were washed twice with 500 ml. of water and twice with 500 ml. of ethanol while still under nitrogen. The product was transferred to a 5.0 l. flask under nitrogen which was then charged with 1.0 l. of ethanol and 972 g (6.00 mol) of diethyl pyrocarbonate. The resulting slurry was then heated to reflux (80° C.) over a period of 1 hr. and maintained at reflux for 4 hrs. Carbon dioxide evolution was rapid for the first 2 hrs. of reflux but appeared to have stopped after 4 hrs. The reaction was then cooled to 5° C. and filtered. The resulting 2,5-dichloro-3,6-bis(carboethoxyamino)-1,4-hydroquinone (III) was washed twice with 500 ml of ethanol and then twice with 500 ml. of water. The water-wet solids were then added over a period of 30 minutes to a vigorously stirred solution of 2.0 l. (31.8 mol) of 70% nitric acid containing 4.0 g of Tergitol 4 (anionic) in a 5.0 l. flask cooled with a water bath at 25° C. Temperatures rose to 35° C. during the addition and solids immediately turned yellow with the evolution of a brown gas ($N_2O_4$). After stirring the reaction for 4 hrs. at 25°-35° C., the product was collected by filtration and washed twice with 500 ml. of deionized water, once with 500 ml. of 0.5M sodium bicarbonate (CAUTION: may be some foaming), twice with 500 ml. water, and once with 500 ml. of absolute ethanol. Drying of the solids in vacuo afforded 505 g (71.9% yield) of 3,6-bis(carboethoxyamino)-2,5-dichloro-1,4-benzoquinone (IV).

EXAMPLE 4

3,6-Bis(Carboethoxyamino)-2,5-Diaziridinyl-1,4-Benzoquinone (V)

In 15.0 l. of THF was dissolved 526.5 g (1.500 mol) of 3,6-bis(carboethoxyamino)-2,5-dichloro-1,4-benzoquinone (IV). To the resulting clear red-orange solution was added 5.0 g of Darco KB and 5.0 g of Darco G-60. After stirring for 1 hr. at 25° C., the charcoal was filtered off through Celite 560. The clear red-orange filtrate was transferred to a 22-l. round-bottom flask and treated successively at 25° C. (water bath) with 606 g (6.00 mol) of triethylamine and 310 ml. (6.00 mol) of ethylenimine. After stirring for 18 hrs. at ambient temperatures, the resulting slurry was cooled to 0°-5° C. (ice-water bath) and stirred for 1 hr. at that temperature. The solids were then collected by filtration and washed three times with 1.5 l. of water to remove the triethylamine hydrochloride and once with 1.5 l. of denatured 200 proof ethanol. Drying the brown solids in vacuo afforded 467 g (85.5% yield) of crude AZQ.

EXAMPLE 5

RECRYSTALLIZATION OF CRUDE AZQ (V)

A 22-l. flask was charged with 16 l. of denatured 200 proof ethanol and heated to 70° C. Then 240 g of crude AZQ was added and the ethanol was heated at reflux (79° C.) to dissolve the AZQ. The hot solution was then filtered and the filtrate was reheated to dissolve the solids which formed after filtration. The solution was then cooled to 0° C. (ice-water bath) and maintained at 0° C. for 1 hr. The crystals were then collected by filtration and washed twice with 500 ml. of 200 proof, denatured ethanol. Drying in vacuo afforded 213 g (88.8% recovery) of AZQ.

EXAMPLE 6

SECOND RECRYSTALLIZATION OF AZQ (V)

A 200-l. flask was charged with 190 lbs. (29 gal., 110 l.) of denatured 200 proof ethanol and heated to 70° C. Then 1.64 kg of once-recrystallized AZQ was added and the ethanol was heated to reflux (79° C.). The reflux was maintained for 15 min. and then the solution was cooled to 0° C. After stirring for 1 hrs. at 0° C., the crystals were collected by filtration and washed twice with 3 l. of denatured, 190 proof ethanol. Drying in vacuo afforded 1.52 kg (92.7% recovery) of AZQ.

NMR: (#619, $CDCl_3$, ppm from internal TMS): 1.29 (t, 6H, $CH_3$), 2.27 (s, 8H, $CH_2$-N), 4.20 (q, 4H, $CO_2CH_2$), 6.28 (broad s, 2H, $\overline{NH}$).

UV: (#395, MeOH): $\lambda_{max}(\epsilon)$: 342 (13,100), 220 (19,700). Lit.[1] $\lambda_{max}(\epsilon)$: 340 mm (14,790).

M.P.: 227° C. (d), Lit.[1]: 230° C. (d).

Karl Fischer: 0.078% $H_2O$.

Weight Loss on Drying: Drying of a 100-mg sample at 100° C. for 4 hrs. over $P_2O_5$ under a vacuum of 0.1 Torr resulted in a weight loss of less than 0.1%.

[1]A. H. Kahn and J. S. Driscoll, *J. Med. Chem.*, 19, 313 (1976).

Ethanol content: The ethanol content was determined to ess than 0.4% by GLC on Porapak T (injection temp=120° C., column temp=115° C.). The sample of AZQ was dissolved in DMSO.

TLC: (#538, Silica Gel): Application of 50, 100γ (0.66% in $CHCl_3$) and elution with EtOAc/$CHCl_3$ (1/1) gave a major spot at $hR_f$15 and a minor spot at the origin ($hR_fO$).

TLC: (#539, Silica Gel): Application of 50, 100γ (0.66% in $CHCl_3$) and elution with $CHCl_3$/MeOH/$N_4OH$ (20/5/1) gave a major spot at $hR_f$75.

Aziridine Titration: The sample was assayed for aziridine groups by titration with acetous perchloric acid in the presence of tetraethylammonium bromide. The sample was dissolved in chloroform and treated with tetraethylammonium bromide prior to titration. The sample was titrated to a potentiometric endpoint. A blank was also run. Based on the theoretical equivalent weight (182.18), the purity was determined to be 97.8%.

| Elemental Analysis: | % C | % H | % N | % O |
|---|---|---|---|---|
| Calcd. for $C_{16}H_{20}N_4O_6$ | 52.75 | 5.53 | 15.38 | 26.35 |
| Found | 52.84 | 5.60 | 15.33 | 25.99 |
| | 52.71 | 5.66 | 15.42 | 25.84 |

The scope of the invention herein shown and described are to be considered only as illustration. It will be apparent to those skilled in the art that numerous modifications may be made therein without departure from the spirit of the invention and the scope of the appended claims.

We claim:

1. The compound of the formula

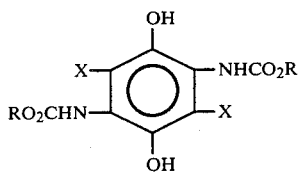

wherein X is chloride, fluoride, bromide, iodide or alkoxy, and R is alkyl, arylalkyl, or phenyl.

2. 2,5-dichloro-3,6-bis(carboalkoxyamino)-1,4-hydroquinone.

3. 2,5-dichloro-3,6-bis(carboethoxyamino)-1,4-hydroquinone.

* * * * *